(12) United States Patent  
Samuels et al.

(10) Patent No.: US 9,198,727 B1  
(45) Date of Patent: Dec. 1, 2015

(54) SURGICAL SPONGE ORGANIZER ASSEMBLY

(71) Applicants: Brenda Samuels, La Quinta, CA (US); Shannon N. Stephens, La Quinta, CA (US)

(72) Inventors: Brenda Samuels, La Quinta, CA (US); Shannon N. Stephens, La Quinta, CA (US)

( * ) Notice: Subject to any disclaimer, the term of this patent is extended or adjusted under 35 U.S.C. 154(b) by 0 days.

(21) Appl. No.: 14/073,000

(22) Filed: Nov. 6, 2013

(51) Int. Cl.
*A61F 15/00* (2006.01)
*A61B 19/02* (2006.01)

(52) U.S. Cl.
CPC ........... *A61B 19/0248* (2013.01); *A61F 15/001* (2013.01)

(58) Field of Classification Search
CPC ......... A61F 15/00; F16B 2/14; A61B 19/029; A61B 19/0248; A61B 19/025; B65D 33/002
See application file for complete search history.

(56) References Cited

U.S. PATENT DOCUMENTS

| | | | |
|---|---|---|---|
| 1,871,240 A * | 8/1932 | Scheller | 403/256 |
| 4,365,709 A | 12/1982 | Lester | |
| 5,022,538 A | 6/1991 | Richmond et al. | |
| 5,114,023 A | 5/1992 | Lavin | |
| 6,505,749 B1 * | 1/2003 | Panetta et al. | 211/86.01 |
| 6,613,036 B1 * | 9/2003 | Farmer et al. | 604/408 |
| 7,641,158 B2 | 1/2010 | Ferguson | |
| D627,063 S | 11/2010 | West et al. | |
| D636,199 S | 4/2011 | Snider | |
| 2002/0096608 A1 | 7/2002 | Cedarberg, III | |
| 2005/0258121 A1 * | 11/2005 | Shea | 211/195 |
| 2007/0267551 A1 | 11/2007 | Townsend | |
| 2012/0132600 A1 * | 5/2012 | Foley | 211/85.15 |

* cited by examiner

*Primary Examiner* — Andrew Perreault

(57) ABSTRACT

A surgical sponge organizer assembly stores and clearly displays surgical sponges after surgery. The assembly includes a hanging panel. A plurality of pouches is attached to a front surface of the hanging panel. Each of the pouches has an open upper end defining an access opening into an interior space of an associated one of the pouches wherein the interior space is configured to store a surgical sponge therein. A support member is configured for being attached to an IV pole. The hanging panel is releasably coupled to the support member.

10 Claims, 5 Drawing Sheets

SURGICAL SPONGE ORGANIZER ASSEMBLY

BACKGROUND OF THE DISCLOSURE

Field of the Disclosure

The disclosure relates to organizer assemblies and more particularly pertains to a new organizer assembly for storing and clearly displaying surgical sponges after surgery.

SUMMARY OF THE DISCLOSURE

An embodiment of the disclosure meets the needs presented above by generally comprising a hanging panel. A plurality of pouches is attached to a front surface of the hanging panel. Each of the pouches has an open upper end defining an access opening into an interior space of an associated one of the pouches wherein the interior space is configured to store a surgical sponge therein. A support member is configured for being attached to an IV pole. The hanging panel is releasably coupled to the support member.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
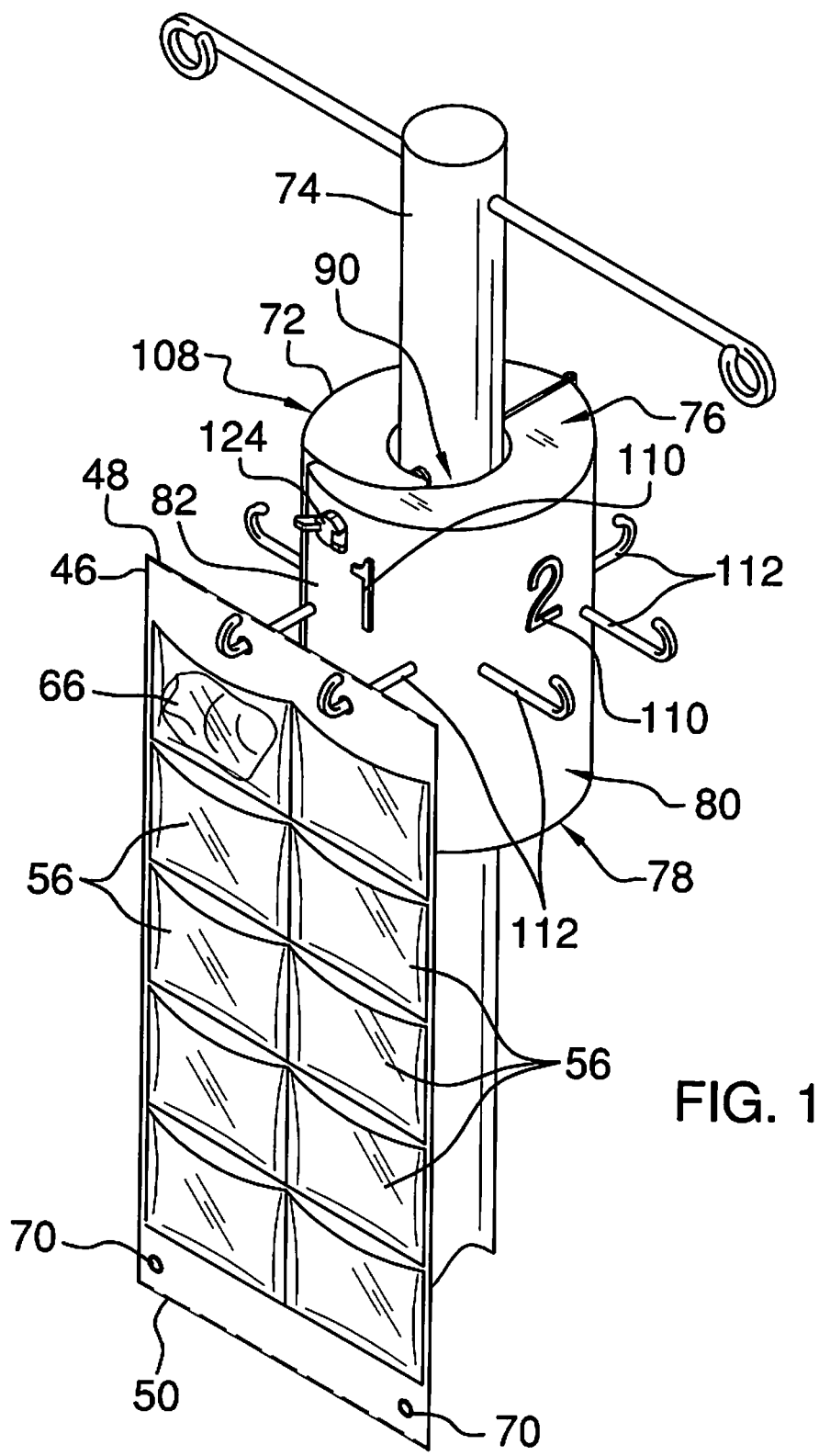
FIG. 1 is a top front side perspective view of a surgical sponge organizer assembly according to an embodiment of the disclosure.
Figure 2:
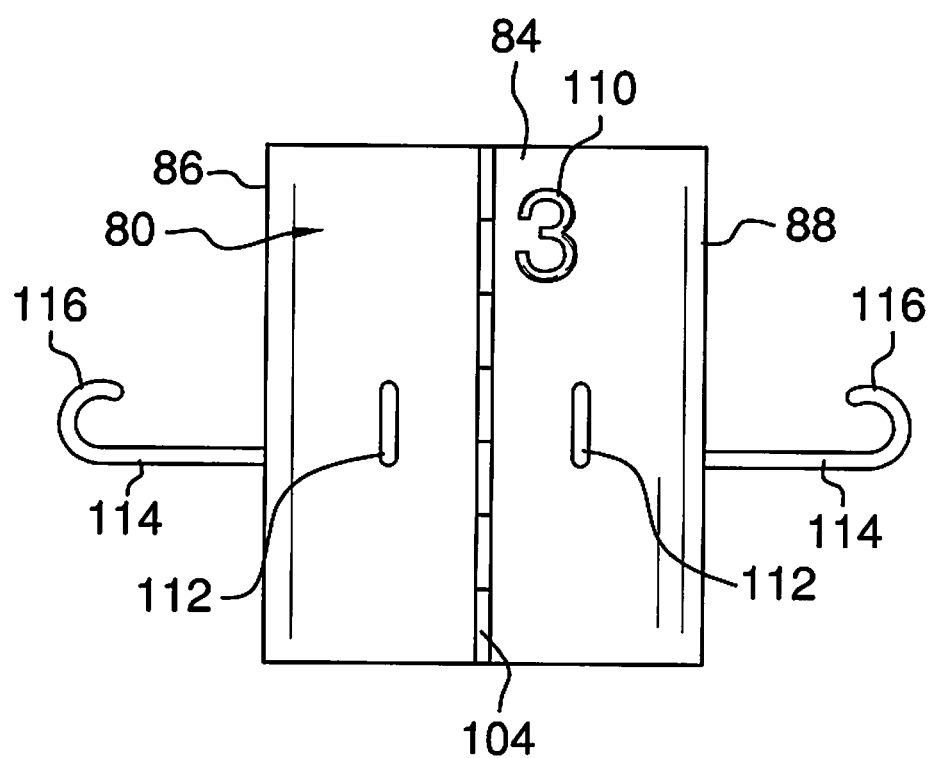
FIG. 2 is a back view of an embodiment of the disclosure.
Figure 3:
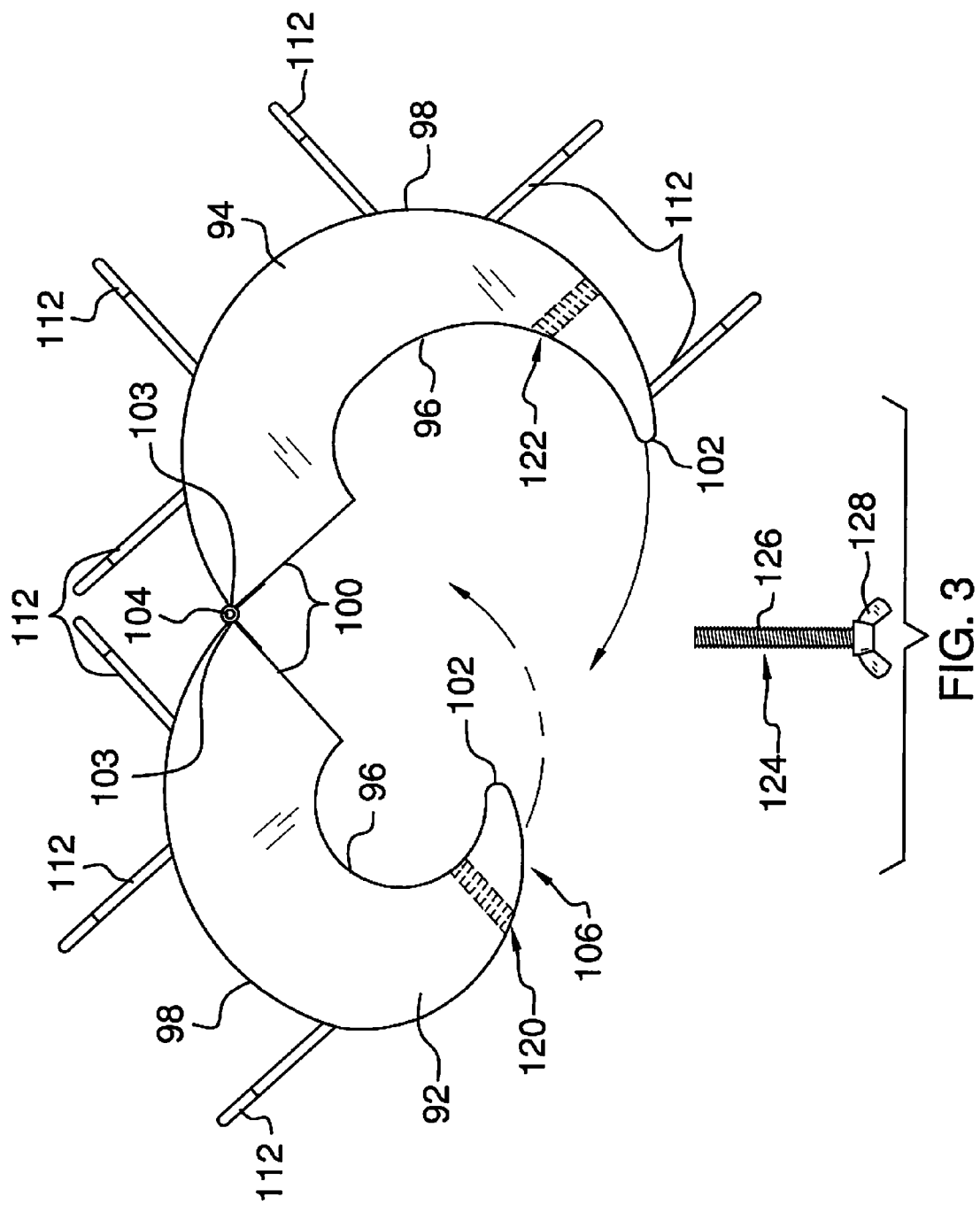
FIG. 3 is a top view of an embodiment of the disclosure.
Figure 4:
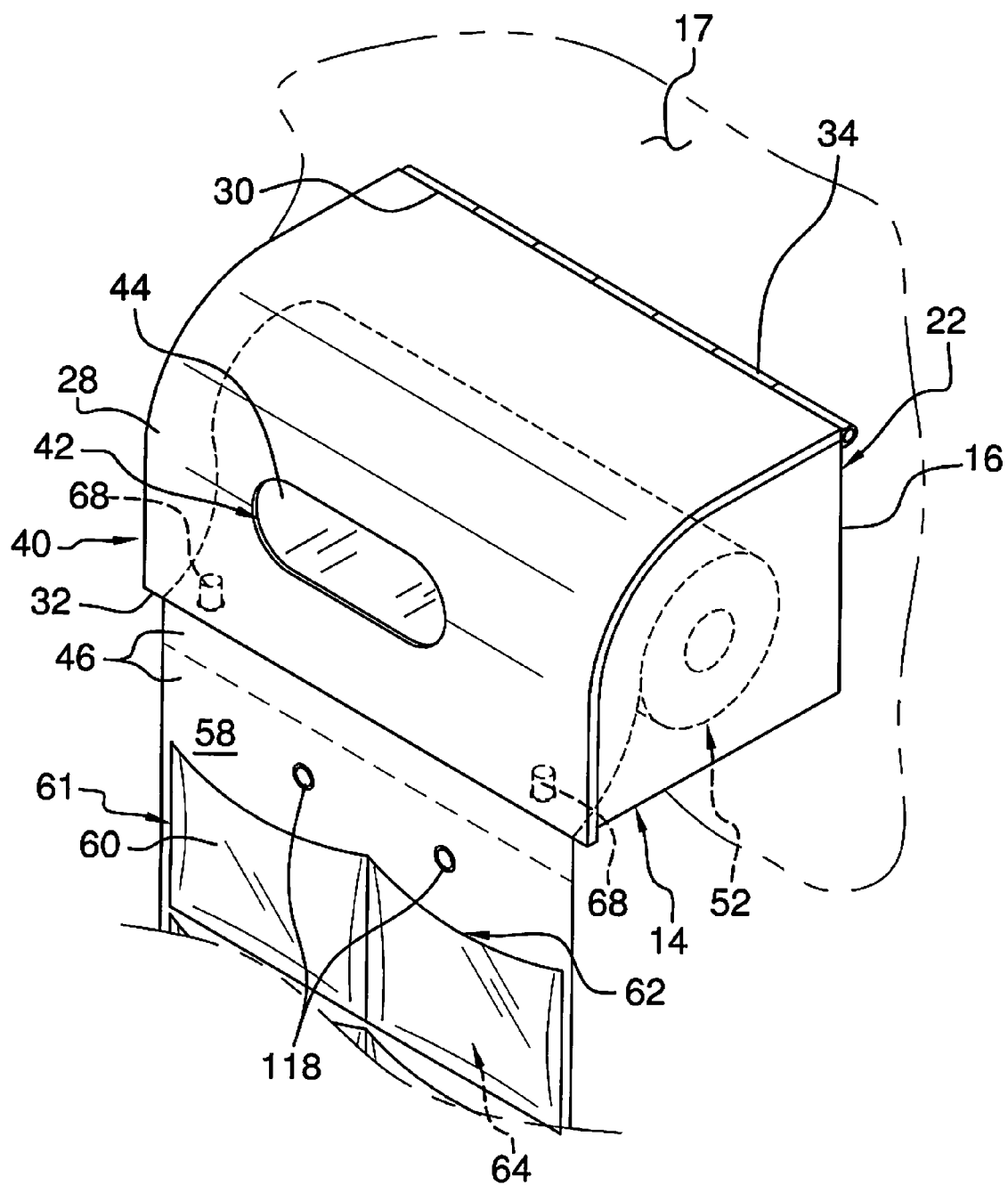
FIG. 4 is a top front side perspective view of an embodiment of the disclosure.
Figure 5:
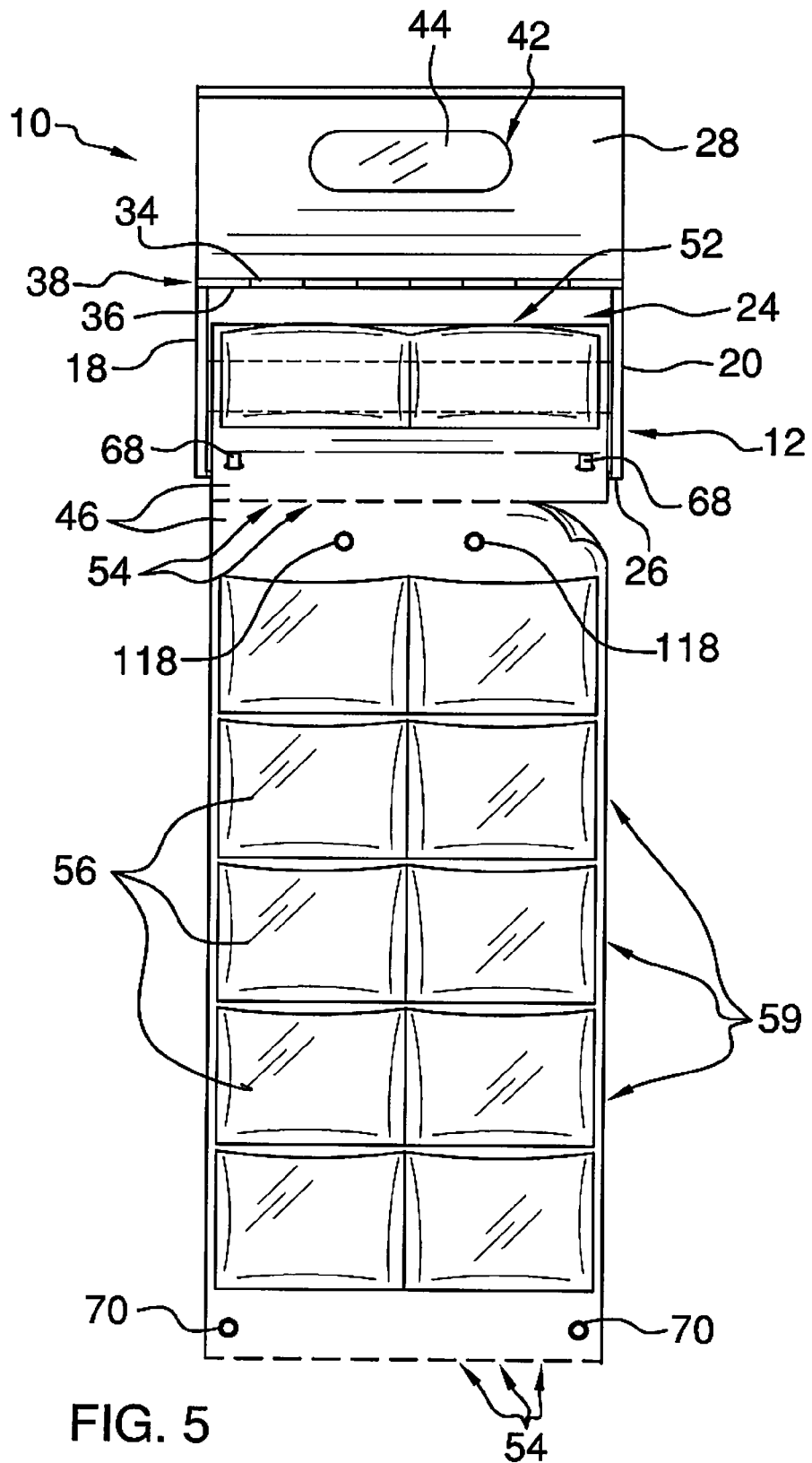
FIG. 5 is a front view of an embodiment of the disclosure.

With reference now to the drawings, and in particular to FIGS. 1 through 5 thereof, a new organizer assembly embodying the principles and concepts of an embodiment of the disclosure and generally designated by the reference numeral 10 will be described.

As best illustrated in FIGS. 1 through 5, the surgical sponge organizer assembly 10 generally comprises a housing 12 having a bottom wall 14 and a perimeter wall 16 attached to and extending upwardly from the bottom wall 14. The housing 12 is configured for mounting to a wall surface 17. The perimeter wall 16 includes a first lateral wall 18, a second lateral wall 20 and a back wall 22 extending between the first 18 and second 20 lateral walls. The housing 12 has an open top 24 extending between the first 18 and second 20 lateral walls and between the back wall 22 and a front edge 26 of the bottom wall 14. The housing 12 may be constructed from plastic or like material.

A lid 28 is coupled to the housing 12. The lid 28 has a top edge 30 and a bottom edge 32. The lid 28 is positionable to cover the open top 24 of the housing 12. The bottom edge 32 of the lid 28 may extend downwardly below the bottom wall 14 of the housing 12 a distance between approximately 0.5 centimeters and 2.5 centimeters. A lid hinge 34 couples the lid 28 and the housing 12. The lid hinge 34 may be positioned between the top edge 30 of the lid 28 and an upper edge 36 of the back wall 22. The lid hinge 34 selectively pivots the lid 28 between an open position 38 exposing the open top 24 of the housing 12 and a closed position 40 covering the open top 24 of the housing 12. A lid opening 42 is positioned in the lid 28. The lid opening 42 may be positioned proximate the bottom edge 32 of the lid 28. A viewing window 44 is positioned in and covers the lid opening 42. The viewing window 44 is translucent wherein the viewing window 44 is configured to permit a viewer to view into the housing 12 when the lid 28 is in the closed position 40. The viewing window 44 may be constructed from plastic or like material.

A plurality of hanging panels 46 is provided. Each of the hanging panels 46 has an upper edge 48 and a lower edge 50. The hanging panels 46 are selectively coupled together to form a roll 52 that is rotatably mountable within the housing 12. Thus, the hanging panels 46 can be rotated outwardly of the housing 12 between the lid 28 and the front edge 26 of the bottom wall 14. The roll 52 has perforations 54 attaching together adjacently positioned ones of the hanging panels 46. The perforations 54 extend along the upper 48 and lower 50 edges of each hanging panel 46 and are configured to permit the hanging panels 46 to be detached from the roll 52.

A plurality of pouches 56 is attached to a front surface 58 of each of the hanging panels 46. The pouches 56 may be arranged into a plurality of rows 59. Each of the pouches 56 has a main section 60 and a perimeter edge 61 attached to and extending around an associated main section 60. The pouches 56 within each of an associated row 59 may be attached together at respective ones of the perimeter edges 61. Each of the pouches 56 has an open upper end 62 defining an access opening into an interior space 64 of an associated pouch 56 wherein the interior space 64 is configured to store a surgical sponge 66 therein. Each of the pouches 56 is translucent wherein the pouches 56 are configured to permit viewing of the surgical sponge 66 positioned within the interior space 64 of the associated pouch 56.

A pair of prongs 68 is coupled to the housing 12. The prongs 68 are spaced and horizontally aligned. The prongs 68 extend upwardly from the bottom wall 14 and are positioned proximate the front edge 26 of the bottom wall 14. A plurality of retaining holes 70 is provided. A spaced pair of the retaining holes 70 is positioned in each of the hanging panels 46. Each of the retaining holes 70 is positioned proximate the lower edge 50 of the associated hanging panel 46. Each of the retaining holes 70 of the associated hanging panel 46 is spaced apart a distance equal to a distance between the prongs 68 wherein the prongs 68 are configured to extend through the retaining holes 70 of the associated hanging panel 46 to retain the roll 52 within the housing 12.

A support member 72 is configured for being attached to an IV pole 74. The support member 72 has a top surface 76, a bottom surface 78, and a perimeter surface 80 coupled to and extending between the top 76 and bottom 78 surfaces. The perimeter surface 80 includes a front side 82, a back side 84, a first side 86 and a second side 88. The first 86 and second 88 sides extend between the front 82 and back 84 sides. The support member 72 defines an aperture 90 extending between the top 76 and bottom 78 surfaces wherein the aperture 90 is configured to receive the IV pole 74 therethrough. In particular, the support member 72 includes a first section 92 and a second section 94. Each of the first 92 and second 94 sections has an inner edge 96, an outer edge 98, a first end 100 and a second end 102. The first 92 and second 94 sections may be attached at a respective outer corner 103 of each of the first ends 100. In particular, each of the first 92 and second 94 sections may be c-shaped. In addition, each of the first ends 100 may be straight, while each of the second ends 102 may be pointed. A longitudinal axis extends through the support member 72 between the top surface 76 and the bottom surface 78. The support member 72 may be constructed from aluminum or like material.

A support member hinge 104 couples the first section 92 to the second section 94 wherein the support member hinge 104 selectively pivots the support member 72 between an open position 106 and a closed position 108. The first ends 100 are positioned to abut each other when the support member 72 is in the closed position 108. The second section 94 has a greater size than the first section 92 wherein the inner edge 96 of the first section 92 is positioned to abut the inner edge 96 of the second section 94 proximate each of the second ends 102 when the support member 72 is in the closed position 108. A plurality of number indicia 110 is positioned on the support member 72. In particular, an associated one of the number indicia 110 may be positioned on each of the front side 82, the back side 84, the first side 86 and the second side 88 of the support number 72. The number indicia 110 may be embossed.

A plurality of hooks 112 is attached to the support member 72. Each of the hooks 112 is spaced and horizontally aligned on the perimeter surface 80 of the support member 72. Each of the front side 82, the back side 84, the first side 86 and the second side 88 may have an associated pair of hooks 112 positioned thereon. Each of the hooks 112 is arcuate and includes a shaft portion 114 and a curved portion 116. Each shaft portion 114 may extend transversely relative to the longitudinal axis of the support member 72.

A plurality of hanging holes 118 is provided. A spaced pair of the hanging holes 118 is positioned in each of the hanging panels 46. Each of the hanging holes 118 is positioned proximate the upper edge 48 of the associated hanging panel 46. Each of the hanging holes 118 of the associated hanging panel 46 is spaced apart a distance equal to a distance between an associated pair of the hooks 112 wherein the hooks 112 are configured to extend through the hanging holes 118 of the associated hanging panel 46 to releasably couple the associated hanging panel 46 to the support member 72.

A first slot 120 extends into the first section 92. The first slot 120 is positioned proximate the second end 102 of the first section 92 and is positioned distally relative to the support member hinge 104. The first slot 120 is threaded. Similarly, a second slot 122 extends into the second section 94. The second slot 122 is positioned proximate the second end 102 of the second section 94 and is positioned distally relative to the support member hinge 104. The second slot 122 is also threaded. The second slot 122 is aligned with the first slot 120 when the support member 72 is in the closed position 108. A fastener 124 is extendable through the first 120 and second 122 slots when the support member 72 is in the closed position 108. The fastener 124 is configured to engage the IV pole 74 to releasably couple the support member 72 to the IV pole 74. The fastener 124 has a shaft 126 and a head 128. The shaft 126 is threaded complementarily relative to the first 120 and second 122 slots.

In use, as stated above and shown in the Figures, the support member 72 is pivoted to the open position 106 and allowed to close around the IV pole 74. The fastener 124 is positioned in the first 120 and second 122 slots and tightened to couple the support member 72 to the IV pole 74. The lid 28 is also pivoted to the open position 38 to allow the roll 52 of hanging panels 46 to be positioned within the housing 12. One of the hanging panels 46 is rotated outwardly of the housing 12, while the retaining holes 70 of an adjacently positioned one of the hanging panels 46 is selectively engaged by the prongs 68 to retain the roll 52 within the housing 12. The hanging panel 46 that is rotated outwardly of the housing 12 is detached from the roll 52 by tearing along the perforations 54 and is then hung on an associated pair of hooks 12. Surgical sponges 66 are placed in each of the pouches 56 on the hanging panel 46 to allow the surgical sponges 66 to be clearly displayed and easily counted after use in surgery. If desired, one hanging panel 46 can be hung on each of the pair of hooks 112 to allow a greater number of surgical sponges 66 to be displayed. In this manner, the assembly 10 simplifies the process of counting surgical sponges 66 after surgery to ensure that all surgical sponges 66 used during surgery are accounted for.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

We claim:

1. A surgical sponge organizer assembly comprising:

a hanging panel;

a plurality of pouches being attached to a front surface of said hanging panel, each of said pouches having an open upper end defining an access opening into an interior space of an associated said pouch wherein said interior space is configured to store a surgical sponge therein;

a support member configured for being attached to an IV pole, said hanging panel being releasably coupled to said support member, a longitudinal axis extending between a top surface and a bottom surface of said support member;

an aperture extending between said top surface and said bottom surface of said support member wherein said aperture is configured to receive the IV pole therethrough;

a fastener being extendable through said support member, said fastener being extendable into said aperture wherein said fastener is configured to engage the IV pole to releasably couple said support member to the IV pole in a fixed position relative to the IV pole;

a plurality of hooks attached to said support member;

a spaced pair of hanging holes being positioned in said hanging panel; and wherein said hooks are configured to extend through hanging holes to releasably couple said hanging panel to said support member.

2. The assembly of claim 1, further comprising each of said pouches being translucent wherein said pouches are configured to permit viewing of the surgical sponge positioned within said interior space of said associated pouch.

3. The assembly of claim 1, further comprising:
wherein said support member includes a first section and a second section;
a support member hinge coupling said first section to said second section wherein said support member hinge selectively pivots said support member between an open position and a closed position.

4. The assembly of claim 3, further comprising each of said first and second sections having an inner edge, an outer edge, a first end and a second end, said first and second sections being attached at a respective outer corner of each of said first ends, said first ends being positioned to abut each other when said support member is in the closed position.

5. The assembly of claim 4, further comprising said second section having a greater size than said first section wherein said inner edge of said first section is positioned to abut said inner edge of said second section proximate each of said second ends when said support member is in the closed position.

6. The assembly of claim 3, further comprising:
a first slot extending into said first section, said first slot being positioned distally relative to said support member hinge;
a second slot extending into said second section, said second slot being positioned distally relative to said support member hinge, said second slot being aligned with said first slot when said support member is in the closed position; and
said fastener being extendable through said first and second slots when said support member is in the closed position.

7. The assembly of claim 6, further comprising:
wherein each of said first and second slot is threaded; and
wherein said fastener has a shaft and a head, said shaft being threaded complementarily relative to said first and second slots.

8. The assembly of claim 1, further comprising:
wherein each of said hooks is arcuate and includes a shaft and a curved portion, each said shaft being extending transversely relative to said longitudinal axis of said support member.

9. The assembly of claim 1, further comprising:
wherein said support member has a top surface, a bottom surface, and a perimeter surface coupled to and extending between said top and bottom surfaces, said perimeter surface including a front side, a back side, a first side and a second side, said first and second sides extending between said front and back sides; and
wherein each of said front side, said back side, said first side and said second side has an associated pair of said hooks positioned thereon, said hanging holes being spaced apart a distance equal to a distance between an associated pair of said hooks.

10. A surgical sponge organizer assembly comprising:
a plurality of hanging panels;
a plurality of pouches, each of said pouches being attached to a front surface of an associated one of said hanging panels, each of said pouches having an open upper end defining an access opening into an interior space of an associated said pouch wherein said interior space is configured to store a surgical sponge therein;
a support member configured for being attached to an IV pole, said hanging panels being releasably coupled to said support member, said support member having a top surface, a bottom surface, and a perimeter surface coupled to and extending between said top and bottom surfaces, said support member defining an aperture extending between said top and bottom surfaces wherein said aperture is configured to receive the IV pole therethrough, wherein said perimeter surface includes a front side, a back side, a first side and a second side, said first and second sides extending between said front and back sides, each of said panels being coupled to a respective one of said front side, said back side, said first side and said second side of said support member; and
a plurality of number indicia being positioned on said support member, an associated one of said number indicia being positioned on each of said front side, said back side, said first side and said second side of said support number, said number indicia being sequential moving around said support member wherein each of said number indicia corresponds to an associated one of said hanging panels.

* * * * *